US00PP37066P2

(12) United States Plant Patent
Ruter

(10) Patent No.: US PP37,066 P2
(45) Date of Patent: Oct. 28, 2025

(54) ***THUJA* PLANT NAMED 'RutThu6'**

(50) Latin Name: *Thuja occidentalis*
Varietal Denomination: RutThu6

(71) Applicant: University of Georgia Research Foundation, Inc., Athens, GA (US)

(72) Inventor: John M. Ruter, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 19/016,885

(22) Filed: Jan. 10, 2025

(51) Int. Cl.
*A01H 5/00* (2018.01)
*A01H 5/12* (2018.01)
*A01H 7/00* (2006.01)

(52) U.S. Cl.
USPC ..... Plt./213
CPC ..... *A01H 7/00* (2013.01); *A01H 5/12* (2013.01)

(58) Field of Classification Search
USPC ..... Plt./213
See application file for complete search history.

*Primary Examiner* — Susan McCormick Ewoldt
*Assistant Examiner* — Zachariah Allan Kay
(74) *Attorney, Agent, or Firm* — Meunier Carlin & Curfman LLC

(57) ABSTRACT

A new and distinct cultivar of *Thuja* plant named 'RutThu6', characterized by its compact, rounding form and yellow foliage with orange tips; growth and heat tolerance in USDA Zone 8a, growth in full sun and afternoon shade conditions in landscape and full sun in container production, disease and insect resistance.

2 Drawing Sheets

Figure 1:
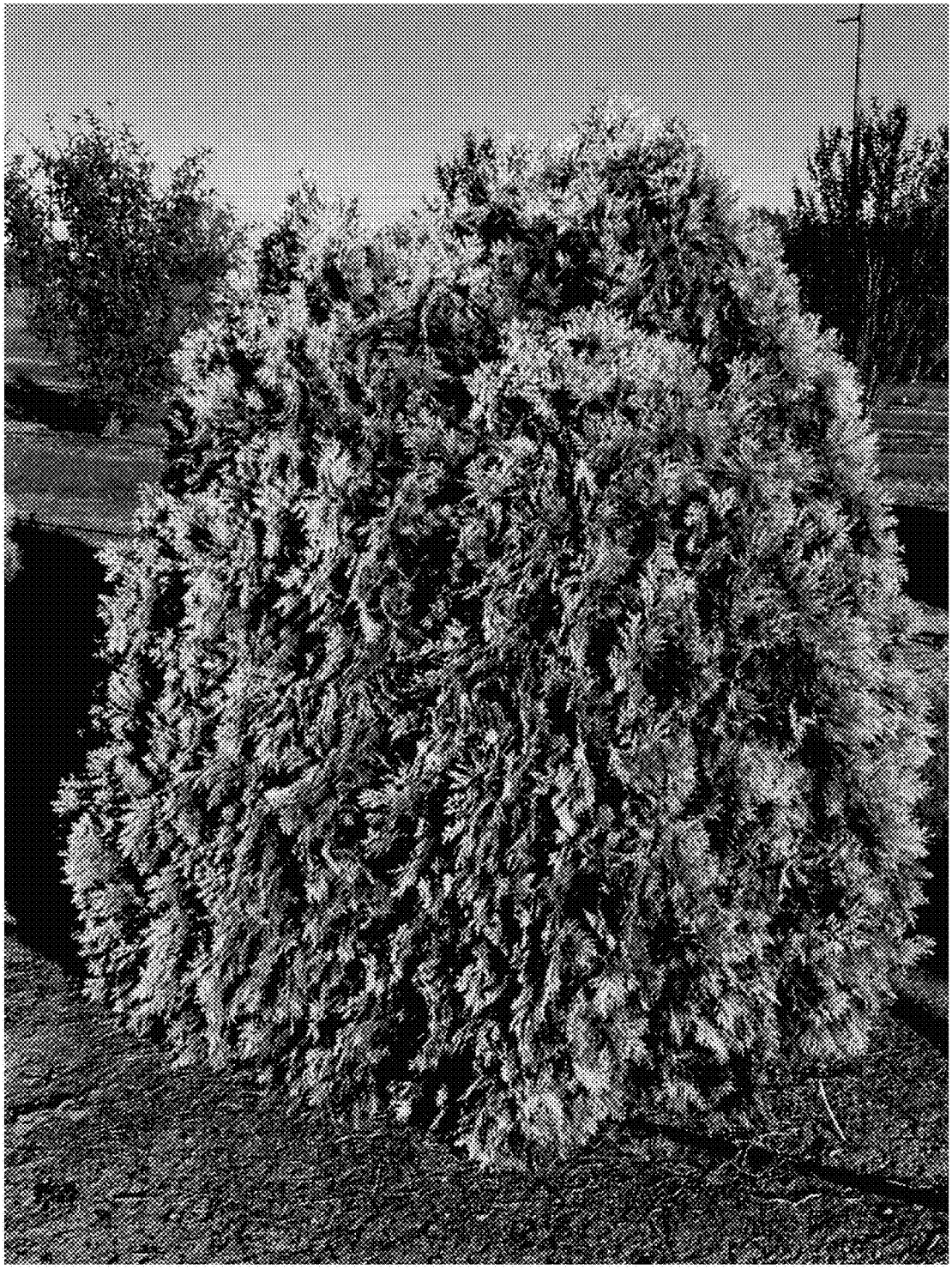

Botanical designation: *Thuja occidentalis.*
Variety denomination: 'RutThu6'.

BACKGROUND

The present invention relates to a new and distinct cultivar of *Thuja*, botanically known as *Thuja occidentalis* and hereinafter referred to by the variety name 'RutThu6'.

The new *Thuja* cultivar 'RutThu6' is a product of open pollination of *Thuja occidentalis* 'Bodmeri' (unpatented female parent). The open-pollinated seeds were obtained from an arboretum in Estonia in 2014. Seedlings were planted in Watkinsville, GA in 2018. The new cultivar 'RutThu6' was selected for its compact, rounded form, yellow foliage turning a greyed-orange on the tips in the winter, very little summer foliage burn in full sun.

Asexual reproduction of the new *Thuja* 'RutThu6' using hardwood cuttings has been continued in Watkinsville, GA since 2018. Observations of the resulting progeny have shown that the unique features of this new *Thuja* 'RutThu6' are stable and reproduced true to type in successive generations.

SUMMARY OF THE INVENTION

The new *Thuja* cultivar 'RutThu6' has not been observed under all possible environmental conditions. The phenotypes may vary somewhat with variations in environment and cultural practices such as temperature, water and fertility levels, soil types, and light intensity without, however, any variance in genotype.

The following traits have been repeatedly observed and are determined to be the unique and distinguishing characteristics of the new *Thuja* cultivar named 'RutThu6'. These characteristics in combination distinguish 'RutThu6' as a new and distinct *Thuja* cultivar:

1. Compact, rounded growth form, compared to the more oval shape of other *Thuja occidentalis* cultivars, such as 'Yellow Ribbon' (unpatented).
2. Yellow foliage turning a greyed-orange on the tips in the winter.
3. Grows and thrives in USDA Zone 8a with no/minimal summer foliage browning of new growth in full sun.
4. Growth in full sun or part-shade in the landscape.
5. Growth in full sun in container production.

Plants of the 'RutThu6' can be compared to similar yellow-foliaged cultivar *Thuja occidentalis* 'Yellow Ribbon' (unpatented) and differs from 'Yellow Ribbon' in that 'RutThu6' has a compact, rounded shape as opposed to oval. 'Yellow Ribbon' has a size (h×w) of about 91"×76" (ratio about 1.2) compared to the more rounded size/shape of 'RutThu6' at about 78"×78" (ratio about 1.0). 'RutThu6' has superior heat tolerance compared to 'Yellow Ribbon' and other yellow-foliaged cultivars that grow in USDA Zone 8a.

The new 'RutThu6' can also be compared to maternal parent *Thuja occidentalis* 'Bodmeri', which has splatterings of white tissue on new growth. In comparison, the new growth of 'RutThu6' has orange-toned tips.

BRIEF DESCRIPTION OF THE PHOTOGRAPHS

The accompanying color photographs illustrate the overall appearance and distinct characteristics of the new cultivar 'RutThu6' showing the colors as true as it is reasonably possible. Colors in the photographs may differ slightly from the color values cited in the detailed botanical description, which accurately describes the colors of 'RutThu6'. The photographs were taken around October 2024 on plants grown outdoors in Watkinsville, Georgia.

The photograph labeled FIG. 1 depicts a side view of a typical 9-year-old 'RutThu6' plant showing the compact, rounded growth form and features and yellow toned foliage.

Figure 2:
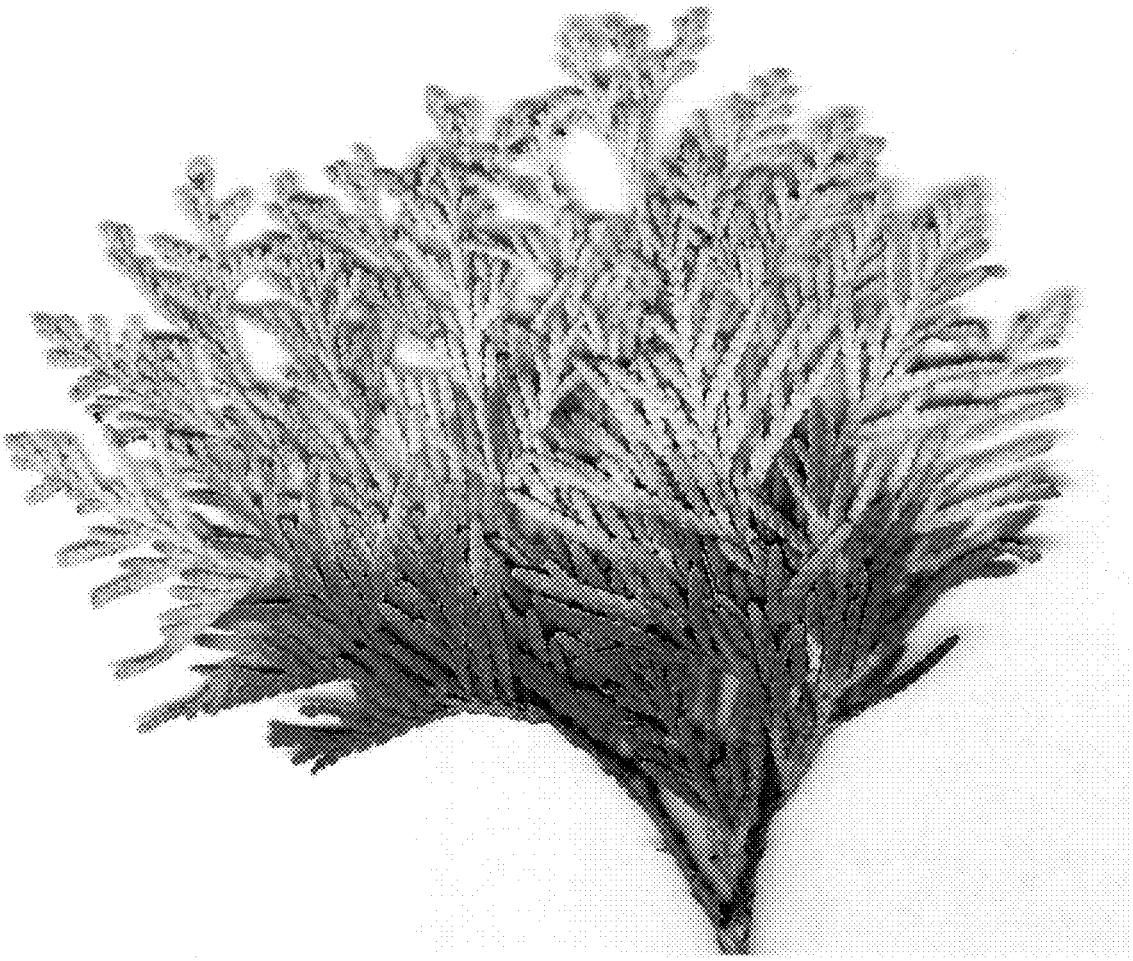

The photograph labeled FIG. 2 depicts a close up view of the branches and needles of a typical 9-year-old 'RutThu6' plant showing the yellow colored foliage and the orange-toned tips of new growth.

DETAILED BOTANICAL DESCRIPTION

The following traits have been consistently observed in the original plants of the new varieties and in asexually propagated progeny grown in Watkinsville, Georgia, (and some in MN) and, to the best knowledge of the inventors, their combination forms the unique characteristics of the new variety 'RutThu6'.

The aforementioned photographs and following observations, measurements, and values describe plants of the cultivar named 'RutThu6'. Data were collected from a horticulture farm in Watkinsville, Georgia from 9-year-old plants. The average temperatures ranged from about 20° F. to 30° F. in the winter and about 90° F. to 100° F. in summer. General light conditions are normal sunlight and numerical values represent averages of typical plant types. The data were collected in December 2023 and August 2024.

Throughout this specification, color names beginning with a small letter signify that the name of that color, as used in common speech, is aptly descriptive. Color names beginning with a capital letter designate values based upon The R.H.S. Colour Chart, 5th edition published by The Royal Horticultural Society, London, England in 2007, except where general terms of ordinary dictionary significance are used.

Botanical classification: *Thuja* 'RutThu6'.

Commercial classification: Ornamental conifer.

Parentage: Open pollination of mixed *Thuja occidentalis* 'Bodmeri' by unknown pollen parents.

Growth and propagation:

- *Propagation type*.—Terminal or sub-terminal hardwood cuttings.
- *Growth rate*.—Slow to moderate.
- *Average growth rate per year*.—About 9 inch height and width increase per year.
- *Root description*.—Typically 2-5 roots arising from the base of the cuttings.
- *Rooting habit*.—Moderate (i.e., about 4-5 roots per cutting).

Plant description:

- *Habit*.—Compact, rounded.
- *Usage*.—Various uses, including landscaping, ornamental, container, border, hedge, and mass planting.
- *Size*.—Height: From soil level to top of plant, about 78 inches. Width: About 78 inches. Ratio of height to width: About 1.0.
- *Number of main trunks*.—About 5 per plant.
- *Average main trunk diameter*.—About 1.25-2 inches at 3 ft above the soil surface.
- *Bark surface texture*.—Smooth.
- *Bark color designation* (*RHS*).—Grayed-green 197B.
- *Winter foliage color* (*RHS*).—Greyed-orange 165B.
- *Branch/stem* (*terminal tuft*).—Quantity: About 9 branchlets per 12 inches of length. Length (of year 1 stem): About 4-9 cm. Base Diameter (of year 2 stem): About 3-4 mm at 15 cm from tip. Branch angle: About 45° from horizontal. Odor (of bruised stem): Mild evergreen. Internode length: About 1.5-2 cm (about 5 internodes per lateral branch). Color (RHS) (of 0.5 year stem): Yellow green 145A to greyed orange 167D. Pubescence: None. Shape: Round.
- *Leaf*.—Leaf type: Scale. Mature size (L×W): About 2 mm×about 2 mm. Arrangement on stem: Decussate. Aspect: Upright. Color (RHS): Upper: Yellow 6A. Lower: Yellow 6C to yellow green 145A. Tips: Yellow orange 17A. Leaf Number: Average of about 12 per cm/stem. Apex: Acute. Base: Rounded. Margin: Entire-Hyaline margin. Shape: Scale. Pubescence: None. Venation: None. Texture: Waxy with abaxial gland. Odor when crushed: Mild evergreen.
- *Long shoots*.—Facial Gland: Present. Leaf Shape: Scale. Color: Greyed orange 167D. Tips: Appressed tips. Apex: Acute.
- *Coning production*.—None observed to date.
- *Seed*.—None observed to date.

Weather/temperature tolerance: Plants of the new *Thuja* have heat tolerance in USDA Zone 8a, with better heat tolerance (e.g., observed tolerance of temperatures up to about 98° F.) than similar yellow-foliaged *Thuja* cultivars, and have a USDA Zone range 3-8. 'RutThu6' thrives in full sun (e.g., observed tolerance of solar radiation up to about 8 kWh per square meter) and afternoon shade in landscape and full sun for container production. 'RutThu6' shows no/minimal summer foliage browning of new growth in full sun.

Disease/pest resistance: To date, plants of the new *Thuja* have not shown any disease or insect issues in field and container trials.

What is claimed is:

1. A new and distinct cultivar of *Thuja* plant named 'RutThu6' as illustrated and described herein.

* * * * *